US012758138B2

(12) United States Patent
Chen et al.

(10) Patent No.: US 12,758,138 B2
(45) Date of Patent: Oct. 13, 2026

(54) ELECTROCARDIOGRAM ("ECG") SIGNAL ANALYSIS

(71) Applicant: Drägerwerk AG & Co. KGaA, Lúbeck (DE)

(72) Inventors: Yu Chen, Andover, MA (US); Haisheng Lu, Andover, MA (US)

(73) Assignee: Drägerwerk AG & Co. KGaA, Lúbeck (DE)

( * ) Notice: Subject to any disclaimer, the term of this patent is extended or adjusted under 35 U.S.C. 154(b) by 324 days.

(21) Appl. No.: 18/444,331

(22) Filed: Feb. 16, 2024

(65) Prior Publication Data

US 2024/0285217 A1 Aug. 29, 2024

Related U.S. Application Data

(60) Provisional application No. 63/447,813, filed on Feb. 23, 2023.

(51) Int. Cl.
*A61B 5/349* (2021.01)
*A61B 5/00* (2006.01)

(52) U.S. Cl.
CPC ............ *A61B 5/349* (2021.01); *A61B 5/7203* (2013.01)

(58) Field of Classification Search
CPC ....... A61B 5/7203; A61B 5/366; A61B 5/316; A61B 5/7221; A61B 5/349; A61B 5/352; A61B 5/7253; A61B 5/725; A61B 5/30; A61B 5/346; A61B 5/7282; A61B 5/308; A61B 5/318; A61B 5/347; A61B 5/33; A61B 5/358; A61B 5/36; A61B 5/0205; A61B 5/339; A61B 5/0022; A61B 5/0053; A61B 5/021; A61B 5/02416; A61B 5/0245; A61B 5/304; A61B 5/35; A61B 5/353; A61B 5/355; A61B 5/4836; A61B 5/7225; A61B 5/7235; A61B 2560/0204; A61B 5/0006; A61B 5/1102; A61B 5/1113; A61B 5/1126; A61B 5/282; A61B 5/7207; A61B 5/721; A61B 5/7239; A61B 5/7257; A61B 5/726; A61B 5/743; A61B 5/746; A61B 5/7475; A61B 5/0507; A61B 5/6805; G16H 50/20; G16H 10/60; G16H 40/67; G01S 7/2886; G01S 7/358; G01S 13/583; G01S 13/56
See application file for complete search history.

(56) References Cited

U.S. PATENT DOCUMENTS

| | | | | |
|---|---|---|---|---|
| 2008/0269813 A1* | 10/2008 | Greenhut | ............. | A61N 1/0504 607/36 |
| 2021/0196139 A1* | 7/2021 | Botzer | ..................... | A61B 5/31 |

FOREIGN PATENT DOCUMENTS

| | | | | |
|---|---|---|---|---|
| CN | 114601437 A * | 6/2022 | ........... | A61B 5/7225 |
| WO | WO-2024062919 A1 * | 3/2024 | ............. | G16H 50/20 |

* cited by examiner

*Primary Examiner* — Devin B Henson
*Assistant Examiner* — Kavya Shobana Balaji
(74) *Attorney, Agent, or Firm* — N. Alexander Nolte; Nolte Lackenbach Siegel

(57) ABSTRACT

A method of processing ECG signals from a plurality of electrocardiogram ("ECG") leads connected to a patient, applying the ECG signals from the ECG leads to a low-pass filter to obtain a low-band filter ("LBF") energy values for the lead and to a high-pass filter ("HBF") to obtain high-band filter energy values for the leads. Running averages of LBF and HBF energy values are utilized to calculate signal-to-noise ("S/N") ratios for the leads. The S/N ratios are used to select two leads for providing ECG signals to an ECG signal processing algorithm.

21 Claims, 5 Drawing Sheets

ELECTROCARDIOGRAM ("ECG") SIGNAL ANALYSIS

CROSS REFERENCE TO RELATED APPLICATIONS

The present application claims priority to and the benefit of U.S. Prov. Pat. App. Ser. No. 63/447,813, which was filed on Feb. 23, 2023, for all purposes, including the right of priority, which application is hereby incorporated herein by reference in its entirety and to the extent that is not inconsistent with the present disclosure.

BACKGROUND

The present discourse relates generally to the field of electrocardiogram ("ECG") signal analysis. More particularly, the present disclosure relates to ECG waveform analysis including artifact detection and rejection, and cardiac signal segment measurements.

Electrocardiogram systems are commonly used to monitor patients' heart conditions as well to detect or predict cardiac events and conditions. In clinical settings, ECG signals are captured in waveforms and analyzed by physiological monitoring devices. The physiological monitoring devices identify systolic intervals, such as QRS-complexes, P-Q intervals, S-T intervals, and the like, which reflect the progression of electrical signals in the heart and corresponding to the depolarization of the right and left ventricles and the contraction of cardiac muscles. For a normal sinus rhythm, an R-wave (a sharp upward deflection) in the QRS-complex with a large amplitude and a small width, is suitable for measuring heart rate and other cardiac conditions. Physiological monitoring devices further classify the detected ECG waveforms into different types, based on features extracted from the morphology of various systolic interval.

In clinical settings, noise contamination caused by artifact signals may adversely impact the precision and accuracy of ECG signal analysis including identification of various systolic intervals and subsequent beat classification. For example, noise contamination may impact the accuracy of algorithms designed to detect several cardiac pathologies such as arrhythmias. As a result, a high rate of false arrhythmia alarms may lead to alarm fatigue, where clinicians may be potentially desensitized to frequent invalid or nonactionable alarms and therefore, silencing the alarms with a risk of missing genuine and critical alarms.

A variety of sources may cause artifact signals, including physiological artifacts caused by patients and non-physiological artifacts caused by electric circuitry in the physiological monitoring devices and/or other devices in the clinical environment. Thus, it is important for physiological monitoring devices to accurately detect artifact signals, identify and analyze the corrupted segments of ECG signals contaminated by artifacts.

SUMMARY

There exists a need for improved detection and analysis of ECG signals, for the physiological monitoring device to identify artifact signals and accordingly, analyze ECG signals in real-time even in the presence of artifacts. There also exists a need for identifying and analyzing systolic intervals in real-time in the presence of noise, for heart rate calculation, beat classification as well as alarm generation.

To resolve at least one or more of the above problems and potentially other present or future problems, one aspect of the present disclosure relates to an apparatus for analyzing ECG signals obtained from a patient monitor including one or more ECG leads coupled to the patient.

The apparatus may include one or more processors configured by machine-readable instructions. The processor(s) may be configured to select a plurality of sample points from in the plurality of sample signals, extract a plurality of features from the selected plurality of sample points and generate a probability of the existence of the artifact signals in the plurality of sample signals, by applying a transformation process to at least two of the plurality of features. The processor(s) may further be configured to apply an algorithm to one or more signals to reliably and accurately detect one or more systolic intervals of the sensed ECG signals.

One or more examples in the present disclosure provide but are not limited to the following advantages. A variety of artifact signals that cause disturbances in ECG monitoring can be detected in real-time. For example, the embodiments in the present disclosure are capable of detecting physiological artifacts caused by patient motion, including motions associated with the patient's medical conditions (e.g., tremors, shivering) and regular muscular activities (e.g., brushing, combing). Additionally, the embodiments in the present disclosure are capable of detecting non-physiological artifacts including electromagnetic interference caused by physiological monitoring systems or other electrical devices in the clinical environment, as well as artifacts caused by cable and/or electrode malfunction. Note that not all embodiments will necessarily exhibit all these advantages nor will they exhibit them to the same degree. Thus, the embodiments in the present disclosure prevent artifact signals from being falsely identified as part of a QRS-complex, thereby increasing the accuracy in QRS-complex identification and classification, as well as the accuracy in heart rate calculation and alarm generation.

On the other hand, when a patient has certain medical conditions, the morphologies of the monitored ECG waveforms can be complex or irregular, and thus, difficult to differentiate from artifact signals. The examples in the present disclosure provide validation processes for identified artifact signals, thereby reducing the false-positive rate. With the complex or irregular ECG waveforms being accurately identified rather than treated as artifacts, the examples in the present disclosure are capable of analyzing different types of ECG waveforms accurately and generating alarms. Thus, clinical providers can promptly identify the medical conditions of the patient and provide treatment as needed, thereby improving clinical workflows.

The above presents a simplified summary in order to provide a basic understanding of some aspects of what is claimed below. This summary is not an exhaustive overview of the claimed subject matter. It is not intended to identify key or critical elements of the disclosure or to delineate the scope of the claims. Its sole purpose is to present some concepts in a simplified form as a prelude to the more detailed description that is discussed later.

BRIEF DESCRIPTION OF THE DRAWINGS

In the drawings, like reference numbers generally indicate identical, functionally similar, and/or structurally similar elements.

Figure 1:
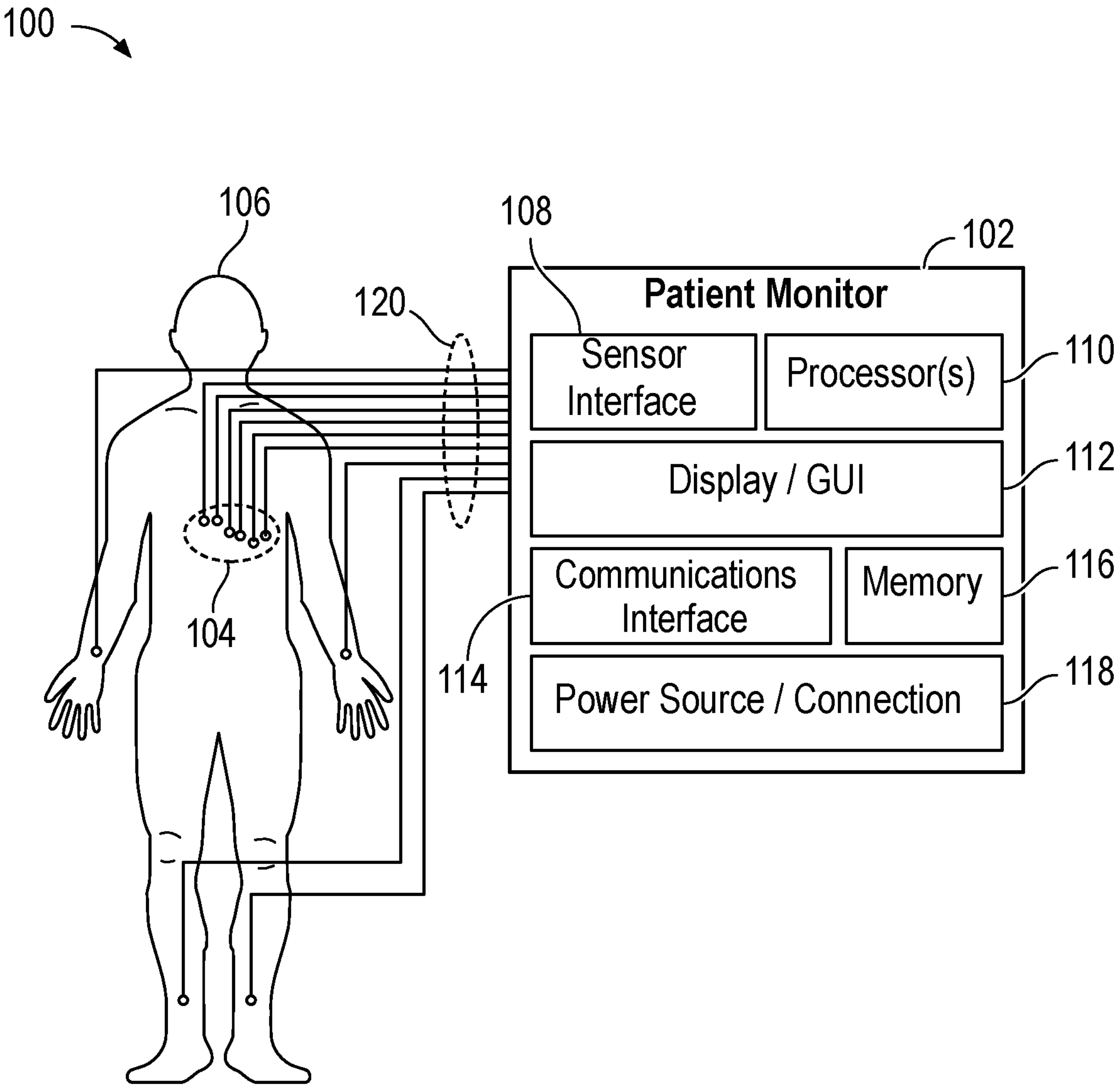
FIG. 1 illustrates a patient monitoring system according to one or more examples.

While the disclosed technique is susceptible to various modifications and alternative forms, the drawings illustrate specific embodiments herein described in detail by way of example. It should be understood, however, that the description herein of specific embodiments is not intended to limit that which is claimed to the particular forms disclosed, but on the contrary, the intention is to cover all modifications, equivalents, and alternatives falling within the spirit and scope of the appended claims.

DETAILED DESCRIPTION

Illustrative examples of the subject matter claimed below are disclosed. In the interest of clarity, not all features of an actual implementation are described for every example in this specification. It will be appreciated that in the development of any such actual implementation, numerous implementation-specific decisions may be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The expressions such as "include" and "may include" which may be used in the present disclosure denote the presence of the disclosed functions, operations, and constituent elements, and do not limit the presence of one or more additional functions, operations, and constituent elements. In the present disclosure, terms such as "include" and/or "have", may be construed to denote a certain characteristic, number, operation, constituent element, component or a combination thereof, but should not be construed to exclude the existence of or a possibility of the addition of one or more other characteristics, numbers, operations, constituent elements, components or combinations thereof.

As used herein, the article "a" is intended to have its ordinary meaning in the patent arts, namely "one or more." Herein, the term "about" when applied to a value generally means within the tolerance range of the equipment used to produce the value, or in some examples, means plus or minus 10%, or plus or minus 5%, or plus or minus 1%, unless otherwise expressly specified. Further, herein the term "substantially" as used herein means a majority, or almost all, or all, or an amount with a range of about 51% to about 100%, for example. Moreover, examples herein are intended to be illustrative only and are presented for discussion purposes and not by way of limitation.

As used herein, to "provide" an item means to have possession of and/or control over the item. This may include, for example, forming (or assembling) some or all of the item from its constituent materials and/or, obtaining possession of and/or control over an already-formed item.

Unless otherwise defined, all terms including technical and/or scientific terms used herein have the same meaning as commonly understood by one of ordinary skill in the art to which the present disclosure pertains. In addition, unless otherwise defined, all terms defined in generally used dictionaries may not be overly interpreted. In the following, details are set forth to provide a more thorough explanation of the embodiments. However, it will be apparent to those skilled in the art that embodiments may be practiced without these specific details. In other instances, well-known structures and devices are shown in block diagram form or in a schematic view rather than in detail in order to avoid obscuring the embodiments. In addition, features of the different embodiments described hereinafter may be combined with each other, unless specifically noted otherwise. For example, variations or modifications described with respect to one of the embodiments may also be applicable to other embodiments unless noted to the contrary.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

A sensor refers to a component which converts a physical quantity to be measured to an electric signal, for example, a current signal or a voltage signal. The physical quantity may for example comprise electromagnetic radiation (e.g., photons of infrared or visible light), a magnetic field, an electric field, a pressure, a force, a temperature, a current, or a voltage, but is not limited thereto.

ECG signal processing, as used herein, refers to, without limitation manipulating an analog signal in such a way that the signal meets the requirements of a next stage for further processing. ECG signal processing may include converting between analog and digital realms (e.g., via an analog-to-digital or digital-to-analog converter), amplification, filtering, converting, biasing, range matching, isolation and any other processes required to make a sensor output suitable for processing.

Turning now to the drawings, FIG. 1 shows a physiological monitoring system 100 according to one or more examples. As shown in FIG. 1, the system includes a patient monitor 102 (e.g., a physiological monitoring device) capable of receiving physiological data from various sensors 104 connected to a patient 106. In this example, sensors 104 comprise ECG electrodes affixed to the skin of patient 106.

In general, it is contemplated by the present disclosure that patient monitor 102 includes electronic components and/or electronic computing devices operable to receive, transmit, process, store, and/or manage patient data and information associated performing the functions of the system, which encompasses any suitable processing device adapted to perform computing tasks consistent with the execution of computer-readable instructions stored in a memory or a computer-readable recording medium.

Further, any, all, or some of the computing devices in patient monitor 102 may be adapted to execute any operating system, including Linux®, UNIX®, Windows Server®, etc., as well as virtual machines adapted to virtualize execution of a particular operating system, including customized and proprietary operating systems. Patient monitor 102 may be further equipped with components to facilitate communication with other computing devices over one or more network connections, which may include connections to local and wide area networks, wireless and wired networks, public and private networks, and any other communication network enabling communication in the system.

As shown in FIG. 1, patient monitor 102 may be, for example, a patient monitor implemented to monitor various physiological parameters of patient 106 via sensors 104. Patient monitor 102 may include a sensor interface 108, one or more processors 110, a display/graphical user interface ("GUI") 112, a communications interface 114, a memory 116, and a power source (or power connection) 118. Sensor interface 108 may be implemented in hardware or combination of hardware and software and is used to connect via wired and/or wireless connections to sensors 104 for gathering physiological data from the patient 106. As noted, sensors 104 in the present example are ECG electrodes affixed to the skin of patient 106. A plurality of conductive leads 120, comprising a plurality of conductive cables, are provided for coupling sensors 104 to sensor interface 108. In one or more examples, conductive leads 120 comprise a plurality of ECG cables.

The data signals from the sensors 104 may include, for example, sensor data related to an ECG. The one or more processors 110 may be used for controlling the general operations of patient monitor 102, as well as processing sensor data received by sensor interface 108. The one or more processors 110 may be, but are not limited to, a central processing unit ("CPU"), a hardware microprocessor, a multi-core processor, a single core processor, a field programmable gate array ("FPGA"), a microcontroller, an application specific integrated circuit ("ASIC"), a digital signal processor ("DSP"), or other similar processing device capable of executing any type of instructions, algorithms, or software for controlling the operation and performing the functions of patient monitor 102.

Display/GUI 112 may be configured to display various patient data, sensor data, and hospital or patient care information, and includes a user interface implemented for allowing interaction and communication between a user and patient monitor 102. Display/GUI 112 may include a keyboard (not shown) and/or pointing or tracking device (not shown), as well as a display, such as a liquid crystal display ("LCD"), cathode ray tube ("CRT") display, thin film transistor ("TFT") display, light-emitting diode ("LED") display, high definition ("HD") display, or other similar display device that may include touch screen capabilities. Display/GUI 112 may provide a means for inputting instructions or information directly to the patient monitor 102. The patient information displayed may, for example, relate to the measured physiological parameters of patient 106 (e.g., ECG readings).

Communications interface 114 may enable patient monitor 102 to directly or indirectly (via, for example, a monitor mount) communicate with one or more computing networks and devices, workstations, consoles, computers, monitoring equipment, alert systems, and/or mobile devices (e.g., a mobile phone, tablet, or other hand-held display device). Communications interface 114 may include various network cards, interfaces, communication channels, cloud, antennas, and/or circuitry to enable wired and wireless communications with such computing networks and devices. Communications interface 114 may be used to implement, for example, a Bluetooth® connection, a cellular network connection, and/or a WiFi® connection with such computing networks and devices. Example wireless communication connections implemented using the communication interface 6 include wireless connections that operate in accordance with, but are not limited to, IEEE802.11 protocol, a Radio Frequency For Consumer Electronics ("RF4CE") protocol, and/or IEEE802.15.4 protocol (e.g., ZigBee® protocol). In essence, any wireless communication protocol may be used.

Additionally, communications interface 114 may enable direct (i.e., device-to-device) communications (e.g., messaging, signal exchange, etc.) such as from a monitor mount to patient monitor 102 using, for example, a universal serial bus ("USB") connection or other communication protocol interface. The communication interface 6 may also enable direct device-to-device connection to other devices such as to a tablet, computer, or similar electronic device; or to an external storage device or memory.

Memory 116 may be a single memory device or one or more memory devices at one or more memory locations that may include, without limitation, one or more of a random-access memory ("RAM"), a memory buffer, a hard drive, a database, an erasable programmable read only memory ("EPROM"), an electrically erasable programmable read only memory ("EEPROM"), a read only memory ("ROM"), a flash memory, hard disk, various layers of memory hierarchy, or any other non-transitory computer readable medium. Memory 116 may be used to store any type of instructions and patient data associated with algorithms, processes, or operations for controlling the general functions and operations of patient monitor 102.

Power source 118 may include a self-contained power source such as a battery pack and/or include an interface to be powered through an electrical outlet (either directly or by way of a monitor mount). Power source 118 may also be a rechargeable battery that can be detached allowing for replacement. In the case of a rechargeable battery, a small built-in back-up battery (or super capacitor) can be provided for continuous power to be provided to patient monitor 102 during battery replacement. Communication between the components of patient monitor 102 in this example (may be established using an internal bus (not explicitly shown in FIG. 1).

Patient monitor 102 may be attached to one or more of several different types of sensors 104 and may be configured to measure and readout physiological data related to patient 106. As noted, sensors 104 may be attached to patient monitor 102 by conductive leads 120 which may be, for example, cables coupled to sensor interface 108. Additionally, or alternatively, one or more sensors 104 may connected to sensor interface 108 via a wireless connection. In which case sensor interface 108 may include circuitry for receiving data from and sending data to one or more devices using, for example, a WiFi® connection, a cellular network connection, and/or a Bluetooth® connection.

The data signals received from sensors 104, may be analog signals. For example, the data signals for the ECG may be input to sensor interface 108, which can include an ECG data acquisition circuit (not shown separately in FIG. 1). An ECG data acquisition circuit may include amplifying and filtering circuitry as well as analog-to-digital (A/D) circuitry that converts the analog signal to a digital signal using amplification, filtering, and A/D conversion methods. In the event that the ECG sensor is a wireless sensor, sensor interface 108 may receive the data signals from a wireless communication module. Thus, sensor interface 108 is a component which may be configured to interface with one or more sensors 104 and receive sensor data therefrom.

As further described herein, the processing performed by an ECG data acquisition circuit may generate analog data waveforms or digital data waveforms that are analyzed by, in this particular embodiment, a microcontroller. However, other embodiments may use other kinds of processors. The microcontroller may be one of the processors 110.

The one or more processors 110, for example, may analyze the ECG waveforms to identify certain waveform characteristics and threshold levels indicative of conditions (abnormal and normal) of the patient 106 using one or more monitoring methods. A monitoring method may include comparing an analog or a digital waveform characteristic or an analog or digital value to one or more threshold values and generating a comparison result based thereon. The microcontroller may be, for example, a processor, an FPGA, an ASIC, a DSP, a microcontroller, or similar processing device. The microcontroller may include a memory or use a separate memory 116. The memory may be, for example, a RAM, a memory buffer, a hard drive, a database, an EPROM, an EEPROM, a ROM, a flash memory, a hard disk, or any other non-transitory computer readable medium.

Memory 116 may store software or algorithms with executable instructions and the microcontroller may execute a set of instructions of the software or algorithms in association with executing different operations and functions of patient monitor 102 such as analyzing the digital data waveforms related to the data signals from sensors 104.

As noted, in the example of FIG. 1, conductive leads 120 between sensors 104 and sensor interface 108 may be an ECG lead set. Conductive leads 120 typically terminate at a sensor 104 that is attached to the patient for measuring ECG data.

As noted, an ECG signal reflects electrical impulses in the heart associated with the systolic rhythm of a beating heart. A normal sinus rhythm includes a repeating succession of "heartbeats" corresponding to heart contractions, and an ECG signal may reflect various phases of such contractions.

Figure 2:
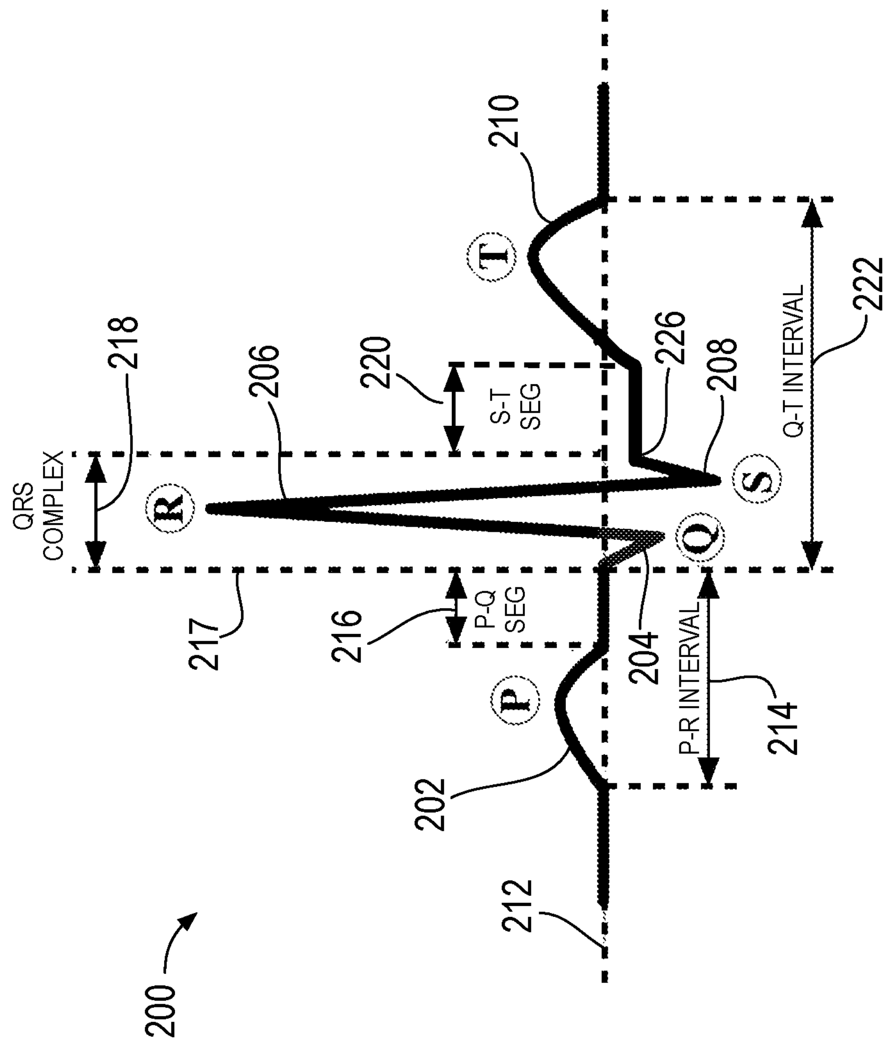
FIG. 2 is a schematic representation of a normal sinus rhythm ECG wave illustrating selected characteristics thereof.

FIG. 2 is a schematic representation of a normal sinus rhythm ECG wave 200. illustrates a sensed ECG signal corresponding to various phases of a single cardiac beat. As shown in FIG. 2, ECG wave 200 includes a plurality of distinct phases corresponding to periods of polarization and depolarization of regions of the cardiac muscle. In particular, ECG wave 200 includes a P-wave 202, a Q-wave 204, an R-wave 206, an S-wave 208, and a T-wave 210. Each of these waves represents either a positive or negative polarization relative to an ECG baseline 212.

A normal sinus rhythm ECG wave such as ECG wave 200 is commonly characterized according to a number of intervals or segments, including, as shown in FIG. 2, a P-R interval 214, a P-Q segment 216, a QRS complex 218, an S-T segment 220, and a Q-T interval 222. A normal sinus rhythm ECG wave such as ECG wave 200 may further be characterized by an "onset" (dashed line 217 in FIG. 2), and a junction point or "J-point" 226. Referring to FIG. 2, J-point 226 in ECG wave 200 is the point where QRS complex 218 joins the S-T segment 220. J-point 226 represents the approximate end of depolarization and the beginning of repolarization. J-point 226 may deviate from baseline 212.

As noted above, noise and artifacts introduced into sensed ECG signals, such as baseline wander caused by motion of the patient or the leads, muscle/electromyographc ("EMG") artifacts, spectrum overlapping with the ECG signal, electrode motion artifacts, respiration artifacts, lead placement artifacts, and so on, which can cause the baseline (such as baseline 212 in FIG. 2) to vary. Variability of the ECG baseline can make it difficult to clinically assess a patient's ECG reading and reliably identify the various waves, intervals, and segments in the sensed ECG waveform.

Referring again to FIG. 1, the one or more processors 110 may further execute processes for performing systolic interval measurements, such as S-T interval measurements, QRS-complex detection, and QRS-complex feature extraction. A QRS-complex is commonly the central and most visually obvious part of an ECG waveform, with a duration of approximately 80 milliseconds (mSec)-100 mSec in adults. Patient monitor 102 may identify the QRS-complex by, for example, identifying an R-wave within the QRS-complex. Processor(s) 110 may search one or more edge points of received sample signals, including a starting point, a peak point, a tail point, and an endpoint. By defining one or more edge points, processor(s) 110 may identify the R-wave and its corresponding QRS-complex.

Concurrently or subsequently, patient monitor 102 may further extract one or more features from the identified QRS-complexes, including but not limited to amplitude, width, morphology, curvature, symmetry, peak direction, intervals of different waves including R-R intervals (i.e., the time interval between two consecutive R-waves), P-R intervals (time interval between the beginning of the upslope of the IP wave to the beginning of QRS wave, and S-T segment measurements. Based on these extracted features, patient monitor 102 may further classify the QRS-complexes into different types, including a normal beat or a bundle branch block beat (N), a ventricular ectopic beat (V), a supraventricular ectopic beat (S), a fusion of ventricular and normal beat (F) and a paced beat or a beat that cannot be classified (Q). Each beat type has its characteristic features and accordingly, physiological monitoring device 102 may store ECG template databases including various pre-determined threshold values or ranges of pre-determined threshold values for each feature. When a new QRS-complex is identified, patient monitor may extract one or more features and compare them with pre-determined threshold values or a ranges of threshold values, thereby classifying the QRS-complex into a specific beat type based on the comparison results.

In other examples, pre-determined threshold values or the ranges of threshold values may be dynamically updated. That is, after a new beat is classified, the extracted features of this beat are used to update the existing QRS-complex template database. When the identified QRS-complex and its corresponding classification indicate cardiac conditions, processor(s) 110 may generate alarms and display one or more extracted features for clinical providers. For example, the duration, amplitude, and morphology of the QRS-complex are useful for clinical providers to diagnose cardiac arrhythmias, conduction abnormalities, ventricular hypertrophy, myocardial infarction, electrolyte derangements, and other cardiac conditions.

In clinical settings, artifact signals are often mixed with ECG signals, which makes it a challenge to systolic event identification, feature extraction, and subsequently, beat classification. For example, an artifact signal with a high amplitude and narrow width (e.g., high-frequency artifacts and low-frequency artifacts) may adversely impact the identification of S-T intervals, R-waves and subsequent feature extraction (e.g., R-R interval, P-R interval, R-wave amplitude, and S-T interval). On the other hand, baseline shift artifacts may corrupt the ECG signals and interfere with the identification and measurement of S-T segments, which are important diagnostic markers for ischemia and infarction.

S-T segment monitoring in particular may enable detection of silent ischemia and result in changes in clinical management. Changes in the S-T segment may also add prognostic information that can potentially influence treatment decisions. Accurate measurement of the elevation of the S-T segment of an ECG waveform is important for detection of myocardial ischemia and infarction in a patient. Therefore, in various examples herein, S-T segment level measurement may be accurately performed in real time by updating an averaged ECG beat cycle waveform in a real time and reliable way, thereby accurately detecting systolic feature points such as J-points and onset points.

Figure 3A:
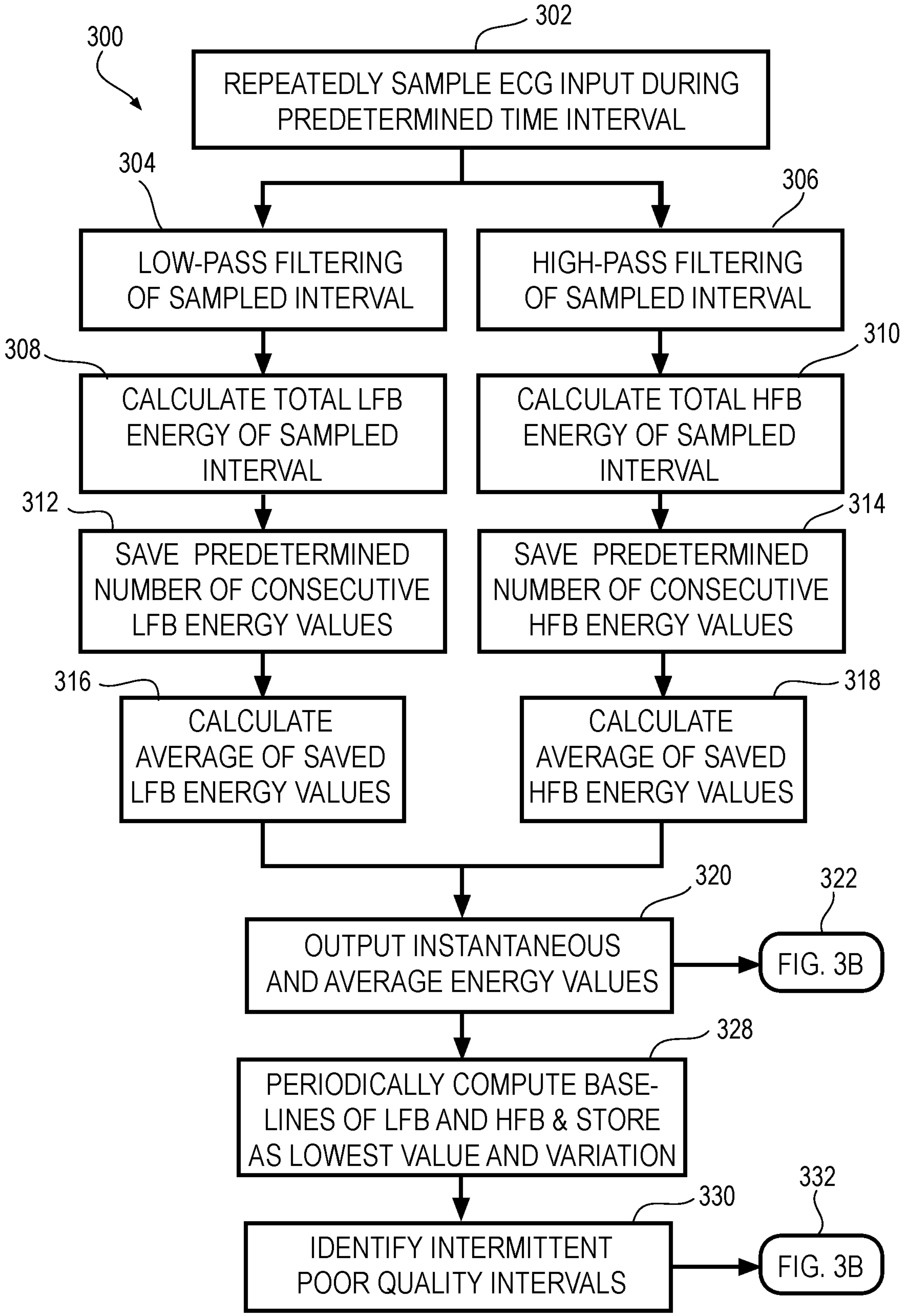
FIGS. 3A and 3B illustrate a flow chart of a method of processing ECG signals according to one or more examples.
Figure 3B:
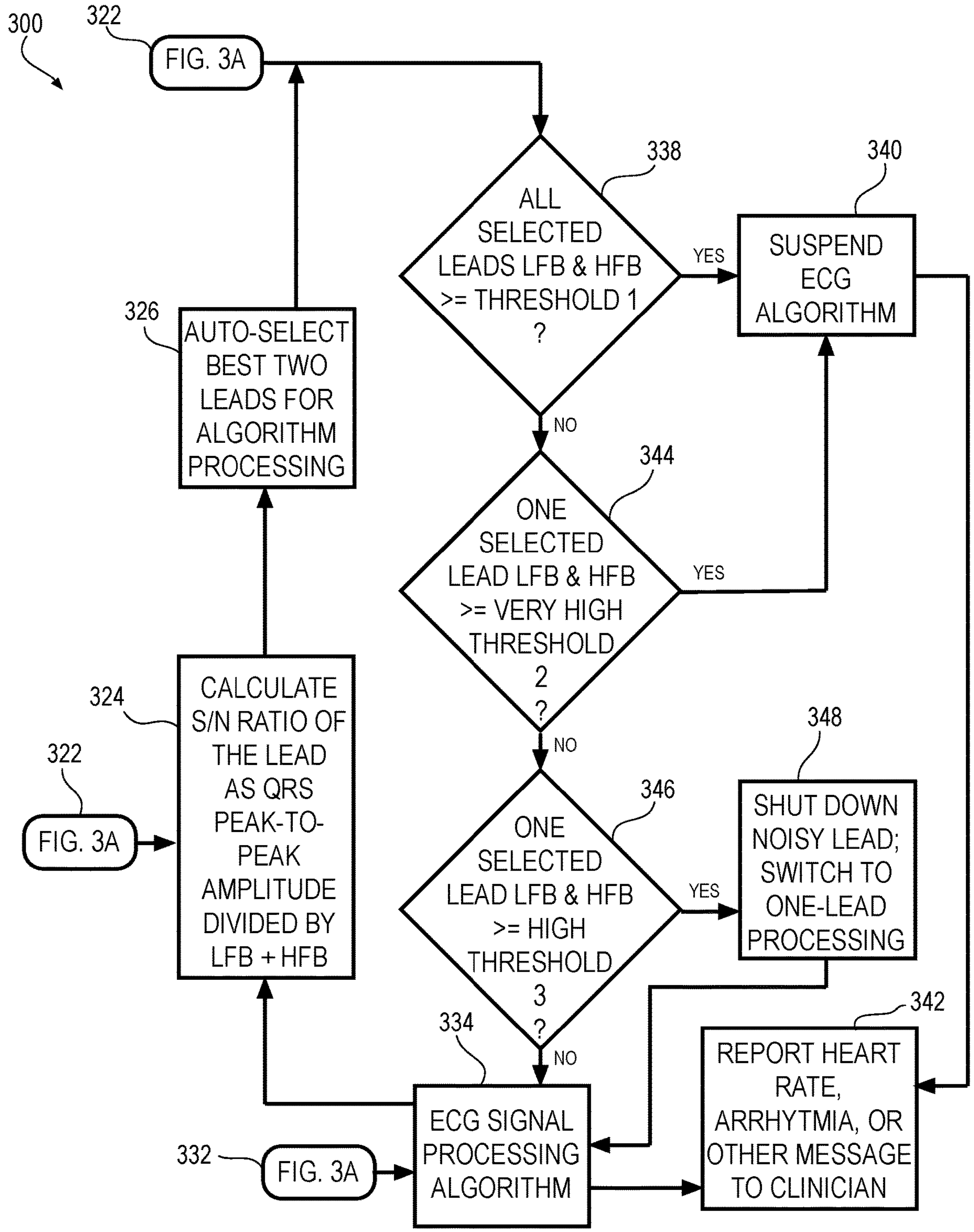

FIGS. 3A and 3B illustrate a method 300 for performing ECG signal processing according to one or more examples. Method 300 may be performed by patient monitor 102, and may be performed independently for each of multiple ECG leads associated with patient monitoring system 100. The steps of method 300 depicted in FIGS. 3A and 3B may be performed in the digital realm, the analog realm, or a combination thereof.

As shown in FIG. 3A, method 300 begins at block 302 repeated sampling of the ECG signal on each ECG lead over a predetermined time interval. In examples, the ECG signal may be sampled 250 times per second over a 300 mSec interval, although different sampling rates and interval durations may be specified. The acquired sampled waveform is subjected to low-pass filtering in block 304 and to high-pass filtering in block 306. The low-pass filtering (block 304) and the high-pass filtering (block 306) may be performed concurrently or sequentially depending on the embodiment. Furthermore, in each of the low-pass filtering (block 304) and the high-pass filtering (block 306), the signals may be filtered concurrently or sequentially depending on the embodiment. Either finite impulse response ("FIR") or Infinite impulse response ("IIR") filters may be utilized. In examples, low-pass filtering may comprise filtering with a bandpass window of less and 1 Hz, and high-pass filtering may comprise filtering with a bandpass window higher than 20 Hz.

Thereafter, the total low-frequency bandpass ("LFB") energy is calculated in block 308, and the total high-frequency bandpass ("HFP") energy is calculated in block 310. The process of sampling the ECG input (block 302), low-pass filtering (block 304), and calculation of LFG and HFB energies (blocks 308 and 310, respectively) may be repeated continuously, such that, in block 312, a plurality of consecutive LFB energy values are stored in an array. For example, eight consecutive values, corresponding to 2.4 seconds of data, may be stored in block 312. Correspondingly, a plurality of consecutive HFB energy values are stored, in block 314.

In block 316, an average of the plurality of LFB energy values saved in block 312 is calculated, while in block 318, an average of the HFB energy values saved in block 314 is calculated. In block 320, the instantaneous LFB energy values and HFB energy values (from blocks 308 and 310, respectively), and the average LFB and HFB energy values (from blocks 316 and 318, respectively) are outputted. As shown by connecting block 322 in FIGS. 3A and 3B, these outputted values are used in block 324 to calculate a signal-to-noise ("S/N") ratio of the lead, by dividing the QRS peak-to-peak amplitude value divided by the sum of the LFB and HFB energy values.

Assuming that method 300 of FIGS. 3A and 3B is being performed independently on multiple leads, then as shown in FIG. 3B, in block 326 a selection is made of the best two leads to be utilized for further ECG processing according to the algorithm described in various examples herein. This selection in block 326 may be made based upon the signals having optimal S/N ratios, for example, S/N ratios greater than 10-12 db. as computed in block 324, for example. That is, in the illustrated example the "best" two leads will be those having the greatest S/N ratios. Other embodiments may use other measures for what is "best".

Referring again to FIG. 3A, method 300 may further involve, in block 328, periodically computing energy baselines of the LFB and HFB energies. These baselines may be computed, for example, in terms of a lowest value and a variation value, i.e., a range of values, for each of the LFB and HFB energy values. The computation step of block 328 may be performed, for example, at 300 mSec intervals based on the past 10- to 20-seconds of averaged data from blocks 316 and 318.

In block 330, intermittent periods of poor ECG signal quality may be identified by comparing the LFB and HFB energy baselines computed in block 328. As shown by connecting block 332 in FIGS. 3A and 3B, this information regarding intermittent poor-quality intervals is provided to a block 334 for performing an ECG signal processing algorithm.

With continued reference to FIG. 3B, execution of the ECG processing algorithm according to one or more examples herein is based upon a selection of leads to be used for that purpose. The selection of leads begins with calculation of S/N ratios for each lead, in block 324 as described above. In examples, the intermittent periods of poor ECG signal quality may be excluded from consideration by the ECG processing algorithm performed in block 334. The ECG algorithm is performed on the beats sensed on the ECG leads selected in block 326. Connecting block 322 in FIG. 3B reflects that the instantaneous and averaged energy values outputted from block 320 in FIG. 3A may be utilized in the assessment of ECG signals provided to the ECG signal processing algorithm (block 334) through a series of threshold assessments (blocks 338, 344, and 346) as herein described.

In particular, as the ECG signal processing algorithm is being performed in block 334, determinations are made, in decision block 338, whether all of the selected leads have LFB and HFB energies which are greater than or equal to a first predetermined threshold. If that is the case, then in block 340, the ECG algorithm is suspended, as this reflects a scenario where the ECG quality is insufficient to be relied upon for making clinical decisions. Upon suspension of the ECG algorithm in block 340, method 300 proceeds to block 342, in which the clinician may be advised of the patient's heart rate, an arrhythmia, S-T interval, or other message.

If all selected leads do not have LFB and HFB energies which exceed the first threshold in block 338, then a further determination is made, in block 344, whether at least one of the selected leads has LFB and HFB energy which exceeds a very high second predetermined threshold, in which case operation proceeds again to block 340, in which the ECG processing algorithm is suspended.

If neither selected lead has LFB and HFB energy exceeding the very high second threshold in decision block 344, then in decision block 346, a determination is made whether one of the selected lead has LFB and HFB energy exceeding a high third predetermined threshold. If not, the normal algorithm operation continues, beginning again at block 334. If one of the selected leads does have LFB and HFB energy exceeding the third high predetermined threshold (which may be lower than the very high first predetermined threshold, this signifies that the lead generating the signal is unsuitably noisy. In that case, in block 348, the noisy lead is shut down and one-lead operation is commenced. A report may be made from block 342 advising the clinician that one-lead operation has commenced.

Figure 4:
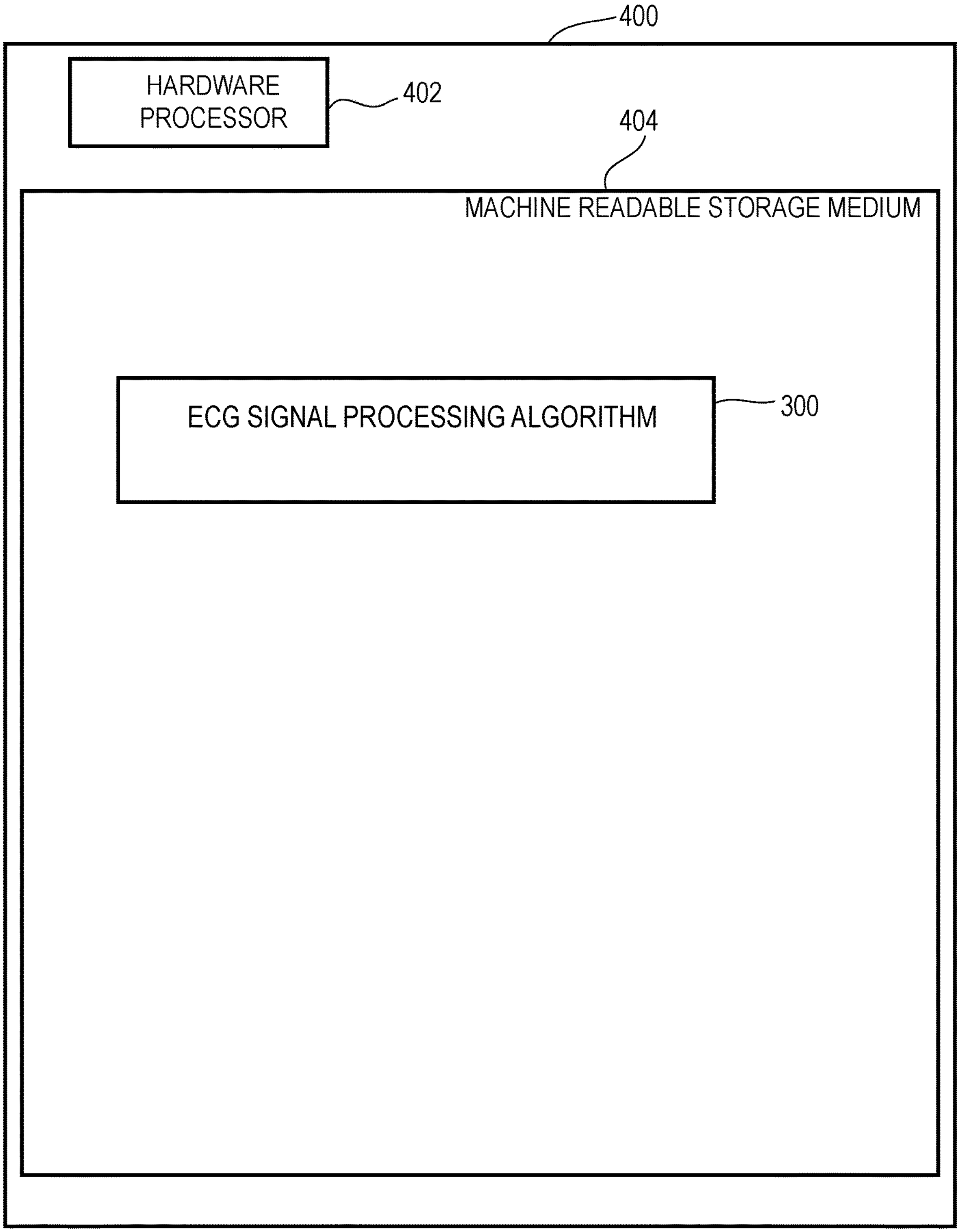
FIG. 4 is a block diagram of a computing resource implementing a method of operating a patient monitoring system according to one or more examples.

FIG. 4 is a block diagram representing a computing resource 400 implementing a method of ECG signal processing according to one or more examples. The computing resource 400 may be, for example and without limitation, a personal desktop computer (e.g., a personal computer), a mobile computing platform (e.g., a laptop or tablet), or a desktop computer accessing cloud computing resources. Computing resource 400 may include at least one hardware processor 402 and a non-transitory machine-readable storage medium 404. As illustrated, machine readable medium 504 may store instructions, that when executed by hardware processor 402 (either directly or via emulation/virtualization), cause hardware processor 402 to perform the method 300 of ECG signal processing described above with reference to FIGS. 3A and 3B.

In various examples, hardware processor 402 may be, for example and without limitation, a microcontroller, a central processing unit ("CPU"), a digital signal processor ("DSP"), a programmed logic array ("PLA"), or a custom processing circuit. Instructions may be executed by one or more processors, such as one or more central processing units ("CPU"), digital signal processors ("DSPs)", general purpose microprocessors, application specific integrated circuits ("ASICs"), field programmable logic arrays ("FPGAs"), or other equivalent integrated or discrete logic circuitry. Accordingly, the term "processor," as used herein refers to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. A "controller," including one or more processors, may use electrical signals and digital algorithms to perform its receptive, analytic, and control functions, which may further include corrective functions. Thus, a controller is a specific type of processing circuitry, comprising one or more processors and memory, that implements control functions by way of generating control signals.

A computer-readable media may be any available media that may be accessed by a computer. By way of example, such computer-readable media may comprise random access memory ("RAM"), read-only memory ("ROM"), electrically-erasable/programmable read-only memory ("EEPROM"), compact disc ROM ("CD-ROM") or other optical disk storage, magnetic disk storage or other magnetic storage devices, or any other medium that may be used to carry or store desired program code in the form of instructions or data structures and that may be accessed by a computer. Disk and disc, as used herein, includes compact disc ("CD"), laser disc, optical disc, digital versatile disc ("DVD"), floppy disk and Blu-ray® disc where disks usually reproduce data magnetically, while discs reproduce data optically with lasers.

Note also that the software implemented aspects of the subject matter hereof are usually encoded on some form of program storage medium or implemented over some type of transmission medium. The program storage medium is a non-transitory medium and may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The claimed subject matter is not limited by these aspects of any given implementation.

The detailed description is made with reference to the accompanying drawings and is provided to assist in a comprehensive understanding of various example embodiments of the present disclosure. Changes may be made in the function and arrangement of elements discussed without departing from the spirit and scope of the disclosure. Various embodiments may omit, substitute, or add various procedures or components as appropriate. For instance, features described with respect to certain embodiments may be combined in other embodiments. In addition, descriptions of well-known functions and constructions may be omitted for clarity and conciseness. Accordingly, those of ordinary skill in the art will recognize that various changes and modifications of the examples described herein can be made without departing from the spirit and scope of the present disclosure.

Use of the phrases "capable of," "capable to," "operable to," or "configured to" in one or more embodiments, refers to some apparatus, logic, hardware, and/or element designed in such a way to enable the use of the apparatus, logic, hardware, and/or element in a specified manner. Use of the phrase "exceed" in one or more embodiments, indicates that a measured value could be higher than a pre-determined threshold (e.g., an upper threshold), or lower than a pre-determined threshold (e.g., a lower threshold). When a pre-determined threshold range (defined by an upper threshold and a lower threshold) is used, the use of the phrase "exceed" in one or more embodiments could also indicate a measured value is outside the pre-determined threshold range (e.g., higher than the upper threshold or lower than the lower threshold). The subject matter of the present disclosure is provided as examples of apparatus, systems, methods, circuits, and programs for performing the features described in the present disclosure. However, further features or variations are contemplated in addition to the features described above. It is contemplated that the implementation of the components and functions of the present disclosure can be done with any newly arising technology that may replace any of the above-implemented technologies.

Various modifications to the disclosure will be readily apparent to those skilled in the art, and the generic principles defined herein may be applied to other variations without departing from the spirit or scope of the present disclosure. Throughout the present disclosure the terms "example," "examples," or "exemplary" indicate examples or instances and do not imply or require any preference for the noted examples. Thus, the present disclosure is not to be limited to the examples and designs described herein but is to be accorded the widest scope consistent with the principles and novel features disclosed.

What is claimed is:

1. A method of processing of electrocardiogram ("ECG") signals from a plurality of ECG leads connected to a patient, comprising:
independently, for each of the plurality of ECG leads:
repeatedly sampling the ECG signal on the lead at a rate of at least 250 times per second over a 300 mSec time interval to obtain a plurality of sample ECG waveforms;
applying each sample waveform to a low-pass filter to obtain a plurality of low-band filter ("LBF") energy values;
applying each sample waveform to a high-pass filter to obtain a plurality of high-band filter ("HBF") energy values;
saving a predetermined number of consecutive LBF energy values and a predetermined number of consecutive HBF energy values for the ECG lead;
calculating a running average of saved LBF energy values and a running average of saved HBF energy values for the ECG lead;
measuring a peak-to-peak amplitude value of a QRS complex in the ECG signals from the ECG lead; and
calculating a signal-to-noise ("S/N") ratio of the ECG lead as a function of the peak-to-peak QRS complex amplitude value divided by the sum of the running average of saved LBF energy values and the running average of HBF energy values;
selecting two of the plurality of ECG leads based on a comparison of the calculated S/N ratio for each of the plurality of ECG leads; and
executing an ECG signal processing algorithm on the ECG signals from the selected leads.

2. The method of claim 1, further comprising:
comparing the LFB energy value and HFB energy value for each of the selected leads to a first predetermined threshold, and if the LFB and HFB energy values for each of the selected leads exceeds the first predetermined threshold, terminating the ECG signal processing algorithm.

3. The method of claim 2, further comprising:
comparing the LFB energy value and HFB energy value for each of the selected leads to a second predetermined threshold, and if the LFB and HFB energy values for one of the selected leads exceeds the second predetermined threshold, terminating the ECG signal processing algorithm.

4. The method of claim 3, further comprising:
comparing the LFB energy value and HFB energy value for each of the selected leads to a third predetermined threshold, and if the LFB and HFB energy values for one of the selected leads exceeds the third predetermined threshold, continuing execution of the ECG signal processing algorithm in a single lead processing mode.

5. The method of claim 4, wherein the third predetermined threshold is greater than the first predetermined threshold, and the second predetermined threshold is greater than the third predetermined threshold.

6. The method of claim 1, further comprising, at the end of each predetermined time interval, computing an energy baseline of the LFB and HFB energy values for each of the plurality of ECG leads as a function of a lowest value and a variation of each of the LFB and HFB energy values.

7. The method of claim 6, further comprising, at the end of each predetermined time interval, identifying periods intermittent poor quality in the ECG signals of each of the plurality of ECG leads based on the computed energy baselines of the LFB and HFB energy values of each of the plurality of ECG leads.

8. A physiological monitoring device, comprising:
a sensor interface configured to receive electrocardiogram ("ECG") signals from a plurality of ECG leads connected to a patient;
at least one processor configured to receive the ECG signals and independently perform ECG signal processing on the ECG signals for each of the plurality of leads;
wherein the ECG signal processing comprises for each ECG lead comprises:
repeatedly sampling the ECG signal of the lead at a rate of at least 250 times per second over a plurality of predetermined intervals to produce a plurality of sample waveforms;
low-pass filtering each sample waveform to obtain a plurality of low-band filter ("LBF") energy values;
high-pass filtering each sample waveform to obtain a plurality of high-band filter ("HBF") energy values;
saving a predetermined number of the LBF energy values and a predetermined number of consecutive HBF energy values;
calculating a running average of saved LBF energy values and a running average of saved HBF energy values for the ECG lead;
measuring a peak-to-peak amplitude value of a QRS complex in the ECG signals from the ECG lead;
calculating a signal-to-noise ("S/N") ratio of the ECG lead as a function of the peak-to-peak QRS complex amplitude value divided by the sum of the running average of saved LBF energy values and the running average of HBF energy values,
and wherein the at least one processor is further configured to:
select two of the plurality of ECG leads based on a comparison of the calculated S/N ratio for each of the plurality of ECG leads; and
execute an ECG signal processing algorithm on the ECG signals from the two selected leads.

9. The physiological monitoring device of claim 8, wherein the at least one processor is further configured to:
compare the LFB energy value and HFB energy value for each of the selected leads to a first predetermined threshold, and if the LFB and HFB energy values for each of the selected leads exceeds the first predetermined threshold, terminate the ECG signal processing algorithm.

10. The physiological monitoring device of claim 9, wherein the at least one processor is further configured to:
compare the LFB energy value and HFB energy value for each of the selected leads to a second predetermined threshold, and if the LFB and HFB energy values for one of the selected leads exceeds the second predetermined threshold, terminate the ECG signal processing algorithm.

11. The physiological monitoring device of claim 10, wherein the at least one processor is further configured to:

compare the LFB energy value and HFB energy value for each of the selected leads to a third predetermined threshold, and if the LFB and HFB energy values for one of the selected leads exceeds the third predetermined threshold, continue execution of the ECG signal processing algorithm in a single lead processing mode.

12. The physiological monitoring device of claim 11, wherein the third predetermined threshold is greater than the first predetermined threshold, and the second predetermined threshold is greater than the third predetermined threshold.

13. The physiological monitoring device of claim 8, wherein the at least one processor is further configured to, at the end of each predetermined time interval, compute an energy baseline of the LFB and HFB energy values for each of the plurality of ECG leads as a function of a lowest value and a variation of each of the LFB and HFB energy values.

14. The physiological monitoring device of claim 13, wherein the at least one processor is further configured to, at the end of each predetermined time interval, identify periods intermittent poor quality in the ECG signals of each of the plurality of ECG leads based on the computed energy baselines of the LFB and HFB energy values of each of the plurality of ECG leads.

15. A computer-readable medium tangibly embodying instructions that, when executed by a processor, perform a method for electrocardiogram ("ECG") signal analysis, comprising:

independently for each of a plurality of ECG leads coupled to a patient:

repeatedly sampling the ECG signal on the lead at a rate of at least 250 times per second for a predetermined time interval to obtain a plurality of sample ECG waveforms;

applying each sample waveform to a low-pass filter to obtain a plurality of low-band filter ("LBF") energy values;

applying each sample waveform to a high-pass filter to obtain a plurality of high-band filter ("HBF") energy values;

saving a predetermined number of consecutive LBF energy values and a predetermined number of consecutive HBF energy values for the ECG lead;

calculating a running average of saved LBF energy values and a running average of saved HBF energy values for the ECG lead;

measuring a peak-to-peak amplitude value of a QRS complex in the ECG signals from the ECG lead;

calculating a signal-to-noise ("S/N") ratio of the ECG lead as a function of the peak-to-peak QRS complex amplitude value divided by the sum of the running average of saved LBF energy values and the running average of HBF energy values;

the method further comprising:

selecting two of the plurality of ECG leads based on a comparison of the calculated S/N ratio for each of the plurality of ECG leads;

executing an ECG signal processing algorithm on the ECG signals from the two selected leads.

16. The computer-readable medium of claim 15, wherein the method further comprises:

comparing the LFB energy value and HFB energy value for each of the selected leads to a first predetermined threshold, and if the LFB and HFB energy values for each of the selected leads exceeds the first predetermined threshold, terminating the ECG signal processing algorithm.

17. The computer-readable medium of claim 16, wherein the method further comprises:

comparing the LFB energy value and HFB energy value for each of the selected leads to a second predetermined threshold, and if the LFB and HFB energy values for one of the selected leads exceeds the second predetermined threshold, terminating the ECG signal processing algorithm.

18. The computer-readable medium of claim 17, wherein the method further comprises:

comparing the LFB energy value and HFB energy value for each of the selected leads to a third predetermined threshold, and if the LFB and HFB energy values for one of the selected leads exceeds the third predetermined threshold, continuing execution of the ECG signal processing algorithm in a single lead processing mode.

19. The computer-readable medium of claim 18, wherein the third predetermined threshold is greater than the first predetermined threshold, and the second predetermined threshold is greater than the third predetermined threshold.

20. The computer-readable medium of claim 15, further comprising, at the end of each predetermined time interval, computing an energy baseline of the LFB and HFB energy values for each of the plurality of ECG leads as a function of a lowest value and a variation of each of the LFB and HFB energy values.

21. The computer-readable medium of claim 20, further comprising, at the end of each predetermined time interval, identifying periods intermittent poor quality in the ECG signals of each of the plurality of ECG leads based on the computed energy baselines of the LFB and HFB energy values of each of the plurality of ECG leads.

* * * * *